United States Patent [19]

Olin

[11] Patent Number: 5,817,364
[45] Date of Patent: Oct. 6, 1998

[54] BEVERAGE CONTAINING ALPHA-KETOGLUTARIC ACID AND METHOD OF MAKING

[75] Inventor: Thomas Olin, Täby, Sweden

[73] Assignee: Gramineer AB, Veddige, Sweden

[21] Appl. No.: 637,666

[22] PCT Filed: Nov. 8, 1994

[86] PCT No.: PCT/SE94/01048

§ 371 Date: Jun. 28, 1996

§ 102(e) Date: Jun. 28, 1996

[87] PCT Pub. No.: WO95/12991

PCT Pub. Date: May 18, 1995

[30] Foreign Application Priority Data

Nov. 9, 1993 [SE] Sweden ................... 9303691-1

[51] Int. Cl.[6] ................... A23L 2/00; A23L 2/39
[52] U.S. Cl. ................... 426/590; 426/72; 426/74; 426/583; 426/656; 426/804; 426/810
[58] Field of Search ................... 426/810, 804, 426/72, 74, 656, 583, 590

[56] References Cited

U.S. PATENT DOCUMENTS

| | | | |
|---|---|---|---|
| 4,001,448 | 1/1977 | Finucane et al. | 426/810 |
| 4,309,417 | 1/1982 | Staples | 426/590 |
| 5,183,674 | 2/1993 | Olin . | |
| 5,270,297 | 12/1993 | Paul et al. | 426/810 |

FOREIGN PATENT DOCUMENTS

| | | |
|---|---|---|
| 39 43 424 A1 | 7/1990 | Germany . |
| 462 463 | 7/1990 | Germany . |
| WO89/03688 | 5/1989 | WIPO . |
| WO90/06064 | 6/1990 | WIPO . |
| WO92/09277 | 6/1992 | WIPO . |
| WO93/23027 | 11/1993 | WIPO . |

OTHER PUBLICATIONS

R.T. Stanko et al., Enhanced Leg Exercise Endurance with a High–Carbohydrate Diet and Dihydroxyacetone and Pyruvate, Am. Psy. Soc., 1990, pp. 1651–1656.

0.48, Muscle Energy Status in Critically Ill Patients Supplemented with Glutamine/Alpha–ketoglutarate, L. Gamrin et al., Dept. of Anesthesiology & Intensive Care, Huddinge Univ. Hosp., Stockholm, Sweden, 1993.

R. Passmore, et al. Handbook on Human Nutritional Requirements, Food and Agriculture Organization of the United Nations, Rome 1974.

Round Table, Round Table on Comparison of Dietary Recommendations in Different European Countries, Second European Nutrition Conference, Munich 1976, Nutr. Metab. 21:210–214.

S. Kirk et al., Role of Arginine in Trauma, Sepsis, and Immunity, Journ of Parenteral and Enteral Nutrition, 1990, vol. 14, No. 5, Supplement, pp. 226S–229S.

T.R. Ziegler, et al.. Potential Role of Glutamine Supplementation in Nutrition Support, Clinical Nutrition, 1993, pp. 82–90.

Gatopro Joins Sports Drink Line, World Food & Drink Report, Oct. 19, 1989, p. N/A, ISSN: 0885–7946.

R.C. Harris et al., Elevation of Creatine in Resting and Excercised Muscle of Normal Subjects by Creatine Supplementation, 93009547/Medline, Clin. Sci. 1992, Sep.;83(3):367–74.

STN International, File Medline, STN accession No. 90190142, Wernerman, J. et al, "Alpha–ketoqlutarate and Postoperative Muscle Catabolism" Lancet, 1990 Mar. 24, 335 (8691) 701–3.

*Primary Examiner*—Helen Pratt
*Attorney, Agent, or Firm*—McDermott, Will & Emery

[57] ABSTRACT

The present invention is related to an energy supply composition particularly suitable for use before, during and after physical exertion. The composition is a beverage, or a dry composition therefore, useful as an energy source in situations which demand a large and rapid energy supply to a healthy mammal including man. The beverage comprises an effective amount of alpha-ketoglutaric acid or a water-soluble innocuous salt thereof together with a nutritionally acceptable water-soluble carrier.

7 Claims, 2 Drawing Sheets

BEVERAGE CONTAINING ALPHA-KETOGLUTARIC ACID AND METHOD OF MAKING

TECHNICAL FIELD

The present invention is related to an energy supply composition particularly suitable for use before, during and after physical exertion.

The object of the invention is to facilitate extended physical exertion by providing energy that is efficiently utilized in mammals. A further object of the invention is to facilitate the accretion of muscle tissue as a result of physical training by sustaining an adequate energy status and permitting rapid build-up of the body's stored energy levels upon rest. A further object is to reduce the loss of water from the body during physical exertion by retaining a high rate of water absorption in the gastrointestinal tract from an energy rich beverage.

BACKGROUND OF THE INVENTION

Individuals undergoing significant physical exertion, whether for athletic or other purposes increase their nutritional needs substantially in order to maintain the body's energy storage and to develop its muscular capacity. If physical training is not accompanied by a proportional increase in nutritional intake, the muscle glycogen depot is not replenished unless proteins, principally from muscle sources, is broken down into constituent amino acids, chiefly alanine and glutamine, to be used as required energy or converted to glucose.

In the last decades, so called sports beverages have enjoyed an increased use by athletes and others doing exercise. Such beverages have largely been based on sugars, salt, minerals and proteins and fragments thereof. For example, in Dialog Abstract No 02331774 (World Food & Drink Report, Oct. 19, 1989) a sports drink named GatorPro is described including water, glucose, soy protein isolate and soy oil. Various attempts have been made to provide a beverage, based on a sound scientific concept, for athletes and other healthy individuals with a high energy demand, e.g. certain convalescents. However, the demand for improved beverages is still great. By a healthy individual in the context of this invention is intended a human and, as applicable, another mammal individual who is not subject to neither in-patient nor out-patient care for conditions relevant herein by a hospital or a medical or veterinary practitioner. Thus the term excludes patients requiring parenteral, or equivalent enteral, supply of the entire or a very large proportion of the energy, electrolyte, fat or amino acid demand of such patient. On the other hand, the term includes those athletes and convalescents just mentioned and other individuals in a similar physical state, although they may have deficiencies or surplus in their body tissues and liquids as compared to an avarage non-diseased and fit individual.

Normally, physical exertion is accompanied by an increase in food intake, and the energy requirements of the intestine, i.e. the small intestine, for digestion are thus also increased in order to provide active transport of substances into the blood stream and to sustain the turnover in epithelial cells that makes up the luminal lining of the intestine. In situations of substantially increased food intake, the intestinal absorption efficiency (i.e. the supply of energy) may be decreased. Thus, an increased demand for energy must be accompanied by a proportionally even higher food intake to avoid metabolic imbalance.

In contrast to some other tissues, the small intestine's primary energy source is the amino acid glutamine. During a meal, glutamine is mainly obtained directly from the food. Between meals, however, glutamine is transported from the muscles, where it is derived from protein breakdown, to the intestine.

In the healthy individual, glutamine is classified as a non-essential nutrient, that is, the body provides enough glutamine to satisfy the metabolic demand for said amino acid. After physical trauma, whether accidental or intentional (e.g. surgery), some non-essential nutrients seem to become semi-essential in order to preserve physical functions such as nitrogen balance and immune function (Kirk S J and Barbul A, JPEN 14, 226–229, 1990; Ziegler T R et al Clin Nutr 12(1), 82–90, 1993). A person in nitrogen balance ingests as much nitrogen (primarily in the form of protein) as is lost in feces, urine and by transpiration. A person in positive nitrogen balance ingests more nitrogen than is lost. External glutamine supply decreases the loss of muscle protein after physical trauma and supports the intestinal barrier against infections caused by microorganisms of the gastrointestinal tract. Due to the chemical instability of glutamine, which cyclesizes to a toxic compound during storage, only a few nutritional products are supplemented with this amino acid.

The main energy depots of the body comprise large molecules synthesized from monomers of glucose, amino acids or fatty acids and glycerol. The formation of these large molecules makes it possible to store a large amount of energy without changing osmotic pressure beyond acceptable limits within the mammal or disturbing substrate and product based regulation of metabolism. On the other hand, the energy depots of the muscle admit a fairly slow inter organ transport of energy. See the Cori cycle, FIG. 1. The Cori cycle is a pathway describing the exchange of fuel molecules and building blocks for biosynthesis, between muscle and liver. The evolution of energy transport cycles and depots is well adjusted to a natural situation of intermittent nutrient intake.

A drawback of the natural energy depot system is the rather inefficient replenishment of the rapid cellular energy sources such as ATP and creatine phosphate from glucose, and the accumulation of metabolic waste products, such as lactic acid. The accumulation of lactic acid, resulting in an obvious oxygen debt, is a well known limiting factor for physical performance. In MEDLINE/93009547 (Clin Sci September 1992; 83(3):367–74) Harris et al show that creatine given as a supplement to normal subjects resulted in an increase in the total creatine content in muscle. However, a larger creatine content does not directly increase the stored energy, but increases the ability to store energy.

The citric acid cycle is the final common pathway for the oxidation of fuel molecules. It also serves as a source of building blocks for biosynthesis. See FIG. 2. Clinical settings on humans and animal studies have suggested that the keto acid α-ketoglutaric acid, a glutamine related metabolite of the citric acid cycle, has an impact similar to glutamine, on the muscle protein balance during stress and medical treatment (Patent SE 462 463, U.S. Pat. No. 5,183,674; Wernerman J. et al, Lancet 335, 701–703, 1990). Intravenous administration of α-ketoglutaric acid, but not glutamine, improves the energy status of the muscle in critically ill patients (Gamrin L, ESPEN 1993, abstract O 48), indicating a metabolic discrepancy between the two nutrients as regards impact on energy status.

In the healthy individual, glucose and fatty acids are the predominant energy substrates for the muscle. During physical exertion glucose is the most rapidly mobilized energy source in skeletal muscle. However, the normal storage capacity of glucose is limited and, more importantly, the muscular work in so-called "fast and medium fast fibres" is not balanced by a corresponding increase in glucose uptake from the blood stream, and such loss of balance causes reduction in the glucose (glycogen) reserve. As the glycogen reserve is diminished, there is an increased utilization of fatty acids in the muscle. The change from glycogen (glucose) to a fatty acid derived energy production is concomitant with a decreased muscular efficiency.

Although the muscle glycogen depot is the predominant carbohydrate source in the working muscle, there is some transport of blood glucose into the muscle. Closer to the point of exhaustion, blood derived glucose becomes increasingly important to the muscle as a carbohydrate source. Nevertheless, the fall in plasma insulin during exercise counteracts the transport of glucose into the muscle, presumably to preserve the blood glucose at a concentration adequate to ensure a well functioning central nervous system.

Pyruvate in combination with dihydroxyacetone increases the muscle uptake of glucose both at rest and during exertion (Stanko R T et al, J Appl Physiol 69(5), 1651–1656, 1990) resulting in an improved leg exercise endurance. In practice, the combination of pyruvate and dihydroxyacetone is not satisfactory due to poor chemical stability.

A typical beverage designed to support energy status during physical exertion is an isotonic aqueous solution which includes traditional food ingredients such as glucose, fructose and galactose and salts. Because of a limited transport of these sugars into the muscle during physical exertion, they are not optimally utilized as energy substrates. Further, even small amounts of sugar tend to delay the water absorption due to decreased water passage through the pylorus. Even a limited loss of water, corresponding to four to five percent of the body weight, results in a marked decrease in muscular work and a concomitant loss of body protein.

BRIEF DESCRIPTION OF THE DRAWINGS

Reference is now made to the drawings accompanying the invention wherein.

DESCRIPTION OF THE INVENTION

Figure 1:
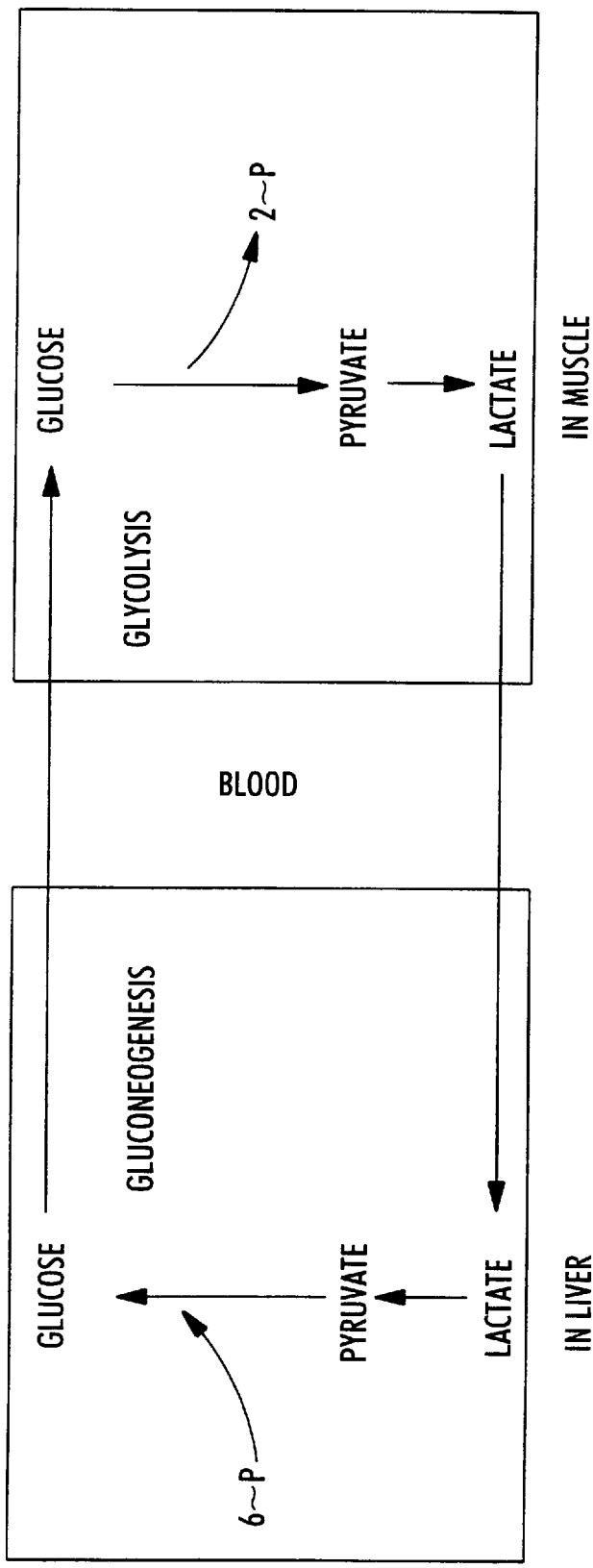
FIG. 1 is a schematic diagram of the Cori cycle.

The present invention provides a beverage, or a dry composition therefor, useful as an energy source in situations with demand of large and rapid energy supply to a healthy mammal including man, comprising an effective amount of α-ketoglutaric acid or a water-soluble innocuous salt thereof together with a nutritionally acceptable water-soluble carrier.

According to another aspect, the invention is related to a method of large and rapid energy supply to a healthy mammal including man, comprising providing to said animal, a beverage, or a dry composition therefor, comprising an effective amount of α-ketoglutaric acid or a water-soluble innocuous salt thereof together with a nutritionally acceptable water-soluble carrier.

According to a further aspect, the invention is related to the use of an effective amount of α-ketoglutaric acid or a water-soluble innocuous salt thereof together with an acceptable water-soluble carrier, for preparation of a beverage, or a dry composition therefor, for use as an energy source in situations with demand of large and rapid energy supply to a healthy mammal including man.

In contrast to sugars such as glucose, the beverage of the invention provides energy with only a minimal increase of water retention in the stomach and will thus counteract the loss of water from the body during physical exertion more efficiently than conventional sugar containing beverages. The enhanced water balance minimizes the loss of body protein during exercise.

Preferred embodiments of the invention will be evident from the following descriptions and claims.

The nutritionally acceptable water-soluble carrier preferably includes one or more of the components: minerals, vitamins, carbohydrates, fat and protein, and is in dry form if the beverage is provided as an extract for dilution. If the beverage is provided ready for consumption it further comprises water. From the stated purpose with the beverage of the invention it will be apparent that the beverage is preferably not intended to fulfil to any substantial degree the requirements of said individual of several free, in particular several essential free, amino acids. The final beverage may have controlled tonicity and acidity, e.g. as a buffered solution. Among further ingredients may be mentioned malic acid, which enhances the rate of energy generating oxidation of α-ketoglutaric acid. Accordingly, the combination of α-ketoglutaric acid and malic acid is one preferred embodiment of the invention. Preferably, the ratio of alpha-ketoglutaric acid to malic acid is 1:0.5 to 1:1.5. Also, preferably, the amount of sugar(s) is below 350 millimoles of monosaccharides per liter.

Two particularly preferred beverages of the invention are as follows:

| Beverage for increasing endurance | |
|---|---|
| Ingredient | Preferred range of content per 100 ml |
| 1. | |
| α-ketoglutaric acid | 0.5–2 g |
| Malic acid* | 0.3–3 g |
| Glucose or a di- or polysaccharide containing glucose | 1–8 g |
| Fructose* | 0.5–1.5 g |
| Sodium, Potassium and Calcium | 0.1–0.5 g |
| Aroma, such as citric acid and/or lime concentrate | 0.5–2.5 g |
| Water | |
| Energy | 10–50 kcal |
| 2. | |
| α-ketoglutaric acid | 1.0–1.5 g |
| Malic acid* | 0.3–3 g |
| Glucose or a di- or polysaccharide containing glucose* | 2–6 g |
| Fructose* | 0.5–1.5 g |
| Sodium, Potassium and Calcium | 0.1–0.5 g |
| Aroma, such as citric acid and/or lime concentrate | 0.5–2.5 g |
| Water | |
| Energy | 10–50 kcal |

*optional

Beverage for Energy Replenishment

In order to provide a nutritiously more complete replenishment after physical exertion the following ingredients may be added to the formula of above described beverages:

| Ingredient | Preferred range of content per 100 ml |
|---|---|
| Lipids and fatty acids* | 0.1–1.0 g |
| Water-soluble protein, e.g. whey protein | 1–5 g |
| Essential minerals according to WHO** | 0.1–0.3 g |
| Vitamins according to WHO** | 0.01–0.1 g |
| Energy | 5–25 kcal |

*optional
**Handbook on Human Nutritional Requirements, Geneva, WHO, Monogr. Serial No 61 (1974), and Nutr. Metab. 21, p 210 (1977).

In contrast to other keto acids α-ketoglutaric acid is stable, and hence suitable for use in beverages. The pH of the beverages is preferably in the range of about 2–5, an in particular about 2–4, to prevent bacterial and fungal growth. Due to the stability of α-ketoglutaric acid the production of a sterilised beverage at a pH of about 6–8 is also possible.

Figure 2:
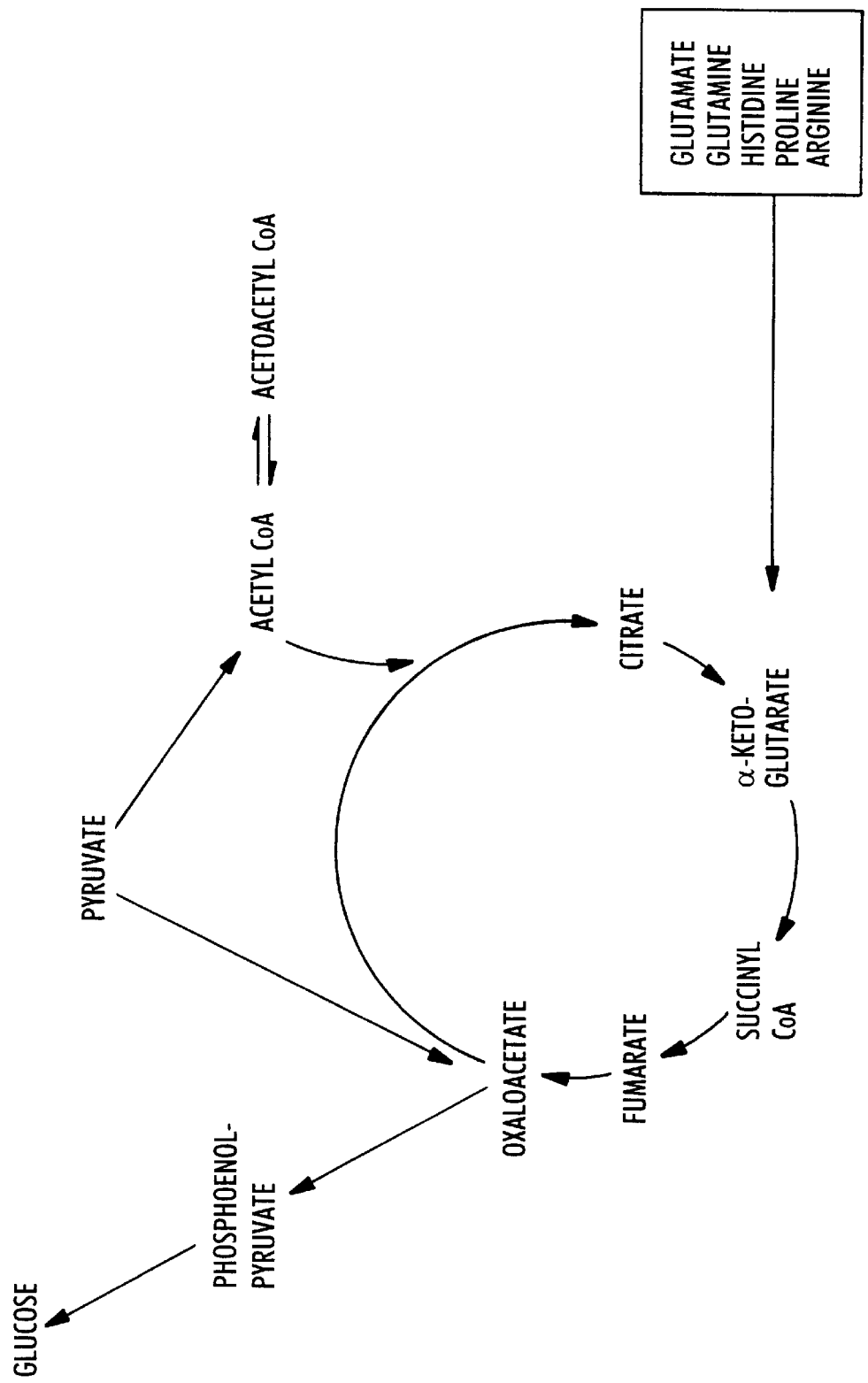
FIG. 2 is a schematic diagram of the citric acid cycle.

The beverage of the present invention provides energy according to the principle of rapid energy recruitment within the organelles of the mammalian cell. An organelle is a sub-cellular compartment representing specialized metabolic function, such as the mitochondria were the formation of energy by oxidative reaction in the citric acid cycle takes place. (See citric acid cycle, FIG. 2). The main energy substrate of the said beverage, α-ketoglutaric acid, is rapidly converted to energy or other metabolites, such as glucose, and a minimum of metabolic waste products. Further, α-ketoglutaric acid stimulates the transport of glucose from the blood into the muscle. The invention will thereby enhance the performance of muscle fibres and save or replenish the indigenous energy depot resulting in an enhanced physical and mental endurance. Also, α-ketoglutaric acid, a constituent in the gluconeogenesis, increases the glycogen deposition when administered before exertion, leading to improved exercise endurance.

α-ketoglutaric acid is formed in each cell that is active in terms of oxidative metabolism and/or amino acid deamination reactions, and is therefore not considered as an essential nutrient. The cells of the intestinal mucosa utilize α-ketoglutaric acid, derived from glutamine, as an energy substrate. This reaction has not, until now, been considered to be limiting for an optimal intestinal function in healthy individuals. Athletes consuming two to four times as much calories as the untrained person, have not been thoroughly studied from such aspect. A further advantage is provided by the invention on the intestinal function exemplified by a sustained absorption efficiency during periods of large food intake, which permits a rapid build-up of the body's stored energy levels upon rest.

Taken together, the improved muscle energy and water supply during physical exertion and the sustained intestinal absorption during periods of large food intake, make the invention facilitate the accretion of muscle tissue as a result of physical training.

The following examples and tests are provided by way of illustration and not by way of limitation.

EXAMPLES OF PREFERRED BEVERAGES

Example 1

| Ingredient | Content per 100 ml |
|---|---|
| α-ketoglutaric acid | 1.2 g |
| Glucose or a di- or polysaccharide of glucose | 2.5 g |
| Fructose | 1.0 g |
| Sodium, Potassium and Calcium | 0.3 g |
| Citric acid and/or lime concentrate | 1.5 g |
| Water | |
| Energy | 19 kcal |

Example 2

| Ingredient | Content per 100 ml |
|---|---|
| α-ketoglutaric acid | 1.5 g |
| Glucose or a di- or polysaccharide of glucose | 4.0 g |
| Fructose | 1.0 g |
| Lipids and fatty acids | 0.1 g |
| Water-soluble protein | 3.0 g |
| Sodium, Potassium and Calcium | 0.3 g |
| Essential minerals according to WHO* | 0.2 g |
| Vitamins according to WHO* | 0.05 g |
| Citric acid and/or lime concentrate | 1.5 g |
| Water | |
| Energy | 39 kcal |

*Handbook on Human Nutritional Requirements, Geneva, WHO, Monogr. Serial No 61 (1974), and Nutr. Metab. 21, p 210 (1977).

STABILITY TEST

Two beverages, A and B, were prepared according to the compositions in example 1 and 2, respectively. Beverage A and B were each divided into four samples and treated as follows:

Sample one: Stored at room temperature for 24 hours.

Sample two: Autoclaved at 120° C. for 25 minutes.

Sample three: Sterilized by heating to 140° C. for 5 seconds (ultra high temperature sterilization, UHT)

Sample four: Sterilized according to sample 3 and then stored at room temperature for 6 months.

The samples were then analyzed for the content of α-ketoglutaric acid, by glutamate dehydrogenase specific NADH oxidation.

RESULTS

After treatment of the samples one, two and three, more than 95 percent of the α-ketoglutaric acid added was recovered from both beverage A and B. When stored for six months (sample four) the content of α-ketoglutaric acid in the two beverages was more than 90 percent of the added amount. The biological value of other ingredients of the beverages were not negatively affected by the presence of α-ketoglutaric acid.

PHYSICAL TESTS

Physical Exertion Program:

Running 6 kilometers three times a week at a speed corresponding to 60–70% of maximal capacity.

50–60 sit-ups and 30–40 arm push-ups four times a week.

Physical Test 1

Study Group

Six healthy men, who on a regular base, practised physical exercise according to the training program above during at least one year prior the onset of the study.

The study were divided into two periods:

I. The test persons practised physical exercise, as described, for one month. During this month they consumed three times 200 ml per day of an energy rich conventional beverage for sportsmen, containing salts and 7.5 g of glucose per 100 ml.

II. The test persons continued their physical exercise according to the protocol for a second month. At the start of this month, they changed from a conventional beverage to consumption of three times 200 ml per day of a beverage according to the present invention (see Example 1)

RESULTS

During study period (I), when provided the conventional beverage, the healthy men did not improve their physical performance. A change to the beverage according to the invention (study period II), was concomitant with an increased physical performance corresponding 10 to 20 percent of average running speed and number of situps and push-ups before exhaustion.

Further, when consuming a beverage according to the invention, the oxygen debt was less pronounced during the day to day intensive short term physical exertion.

As the conventional sugar containing beverage was consumed, close to and during physical exertion, a heavy stomach revealed a slow absorption of the liquid. In contrast, the beverage composed according to the present invention was effectively absorbed when used closed to and during exertion.

Physical Test 2

Six healthy men performing a weekly physical exercise as described in Physical Test 1 were provided with a beverage according to the present invention during a period of six months. The beverage was composed according to Example 1, except from a varying content of α-ketoglutaric acid between 0.01 and 3.5 gram per 100 ml and malic acid in relation thereto. The different beverages were kept isocaloric by compensating the varying content of organic acids with a proportional amount of glucose.

RESULTS

The test persons reported an enhanced endurance during physical exertion when consuming a beverage including 0.1 to 2.5 g of α-ketoglutaric acid per 100 ml. Immediately after exercise, the consumption of a beverage containing a combination of α-ketoglutaric acid and malic acid, resulted in a significantly faster energy boost as compared to a beverage containing α-ketoglutaric acid alone.

Physical Test 3

Study Group

Six well trained long distance runners joined the study during a training period according to the Physical Exertion Program above. The athletes were provided a beverage of the invention according to Example 2. During a study period of one month, they consumed 600 to 800 ml per day of the beverage.

RESULTS

The athletes recorded an increased training tolerance the day after heavy exercise, as a retained endurance. The onset of muscle fatigue during physical exercise was postponed and correlated to a decreased accumulation of lactic acid. Further, the athletes interpreted part of the impact of the beverage on physical performance, as a rapid build-up of the body's stored energy levels upon rest. The increased training tolerance in combination with a high level of stored energy minimize the combustion of amino acids and thus facilitates, accretion of muscle protein and development of muscle performance.

I claim:

1. A beverage, or a dry composition therefor, providing an energy source in situations with demand of large and rapid energy supply to a healthy mammal comprising 0.1 to 2.5 percent of the wet weight of α-ketoglutaric acid or a water-soluble innocuous salt thereof together with a nutritionally acceptable water-soluble carrier.

2. A beverage, or a dry composition therefor, according to claim 1, wherein α-ketoglutaric acid is combined with malic acid.

3. A beverage according to claim 2, wherein the ratio α-ketoglutaric acid:malic acid is 1:0.5 to 1:1.5.

4. A beverage, or a dry composition therefor, according to claim 1, comprising an acid and heat stable whey protein concentrate making up a 1 to 20 percent visually clear water solution.

5. A beverage according to claim 1 wherein the nutritionally acceptable water-soluble carrier includes at least one of the components: water, minerals, vitamins, organic acids, carbohydrates, fat and protein in a water-soluble form.

6. A beverage according to claim 1, wherein the beverage further includes sugar(s) in amounts below 350 millimoles of monosaccharides per liter.

7. A method of large and rapid energy supply to a healthy mammal, comprising providing to said animal, a beverage, or a dry composition therefor, comprising 0.1 to 2.5 percent of the wet weight of α-ketoglutaric acid or a water-soluble innocuous salt thereof together with a nutritionally acceptable water-soluble carrier.

* * * * *